(12) United States Patent
Tsuchiya

(10) Patent No.: US 8,817,251 B2
(45) Date of Patent: Aug. 26, 2014

(54) DEFECT INSPECTION METHOD

(71) Applicant: Noriaki Tsuchiya, Tokyo (JP)

(72) Inventor: Noriaki Tsuchiya, Tokyo (JP)

(73) Assignee: Mitsubishi Electric Corporation, Tokyo (JP)

(*) Notice: Subject to any disclaimer, the term of this patent is extended or adjusted under 35 U.S.C. 154(b) by 0 days.

(21) Appl. No.: 13/673,298

(22) Filed: Nov. 9, 2012

(65) Prior Publication Data
US 2013/0235373 A1 Sep. 12, 2013

(30) Foreign Application Priority Data

Mar. 12, 2012 (JP) ................. 2012-054213

(51) Int. Cl.
G01N 21/00 (2006.01)
G01N 21/95 (2006.01)
G01N 21/956 (2006.01)

(52) U.S. Cl.
CPC .......... *G01N 21/9501* (2013.01); *G01N 21/956* (2013.01)
USPC ..................................... 356/237.5

(58) Field of Classification Search
CPC ................................. G01N 21/9501
USPC .............. 356/237.5, 601; 348/126.5
See application file for complete search history.

(56) References Cited

U.S. PATENT DOCUMENTS

| 6,140,654 A | 10/2000 | Nakasugi et al. | |
|---|---|---|---|
| 7,629,993 B2 * | 12/2009 | Harless et al. | 348/126 |
| 2005/0254065 A1 * | 11/2005 | Stokowski | 356/601 |
| 2007/0023932 A1 | 2/2007 | Sogawa et al. | |
| 2007/0146697 A1 * | 6/2007 | Noguchi et al. | 356/237.5 |

FOREIGN PATENT DOCUMENTS

| JP | 63-222438 | 9/1988 |
|---|---|---|
| JP | 2000-200358 A | 7/2000 |

* cited by examiner

*Primary Examiner* — Tarfur Chowdhury
*Assistant Examiner* — Md Rahman
(74) *Attorney, Agent, or Firm* — Studebaker & Brackett PC

(57) ABSTRACT

A defect inspection method according to the present invention is a defect inspection method for inspecting a defect of a semiconductor wafer, including the steps of: (a) forming a mark on a semiconductor wafer that is an inspection object, the mark corresponding to the size of a device chip that will be obtained from the semiconductor wafer, the mark being formed with respect to a predetermined device chip on the semiconductor wafer; and (b) during a predetermined process included in a semiconductor wafer process or before the semiconductor wafer process, performing a defect inspection on the semiconductor wafer and recognizing defect information based on the mark as a reference.

10 Claims, 2 Drawing Sheets

F I G. 1
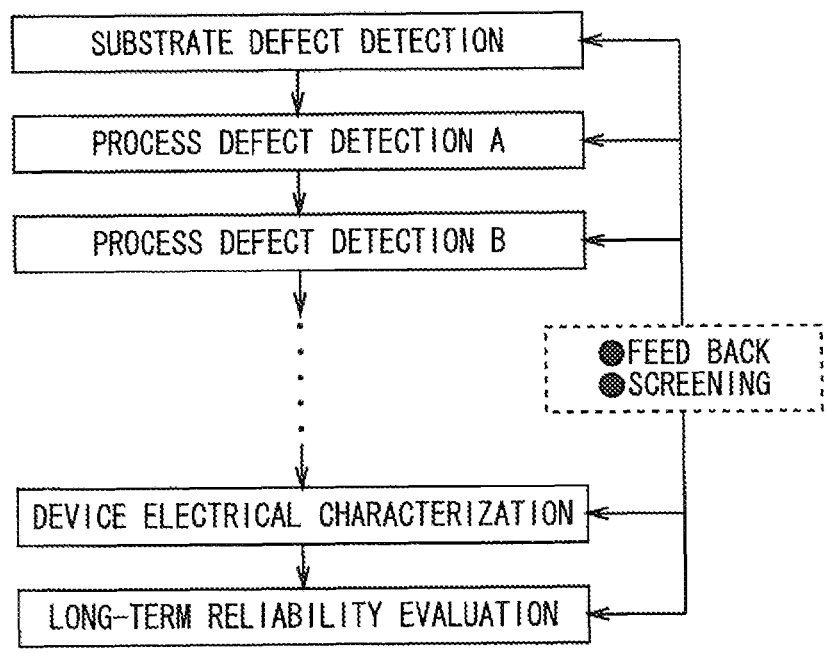
F I G. 2
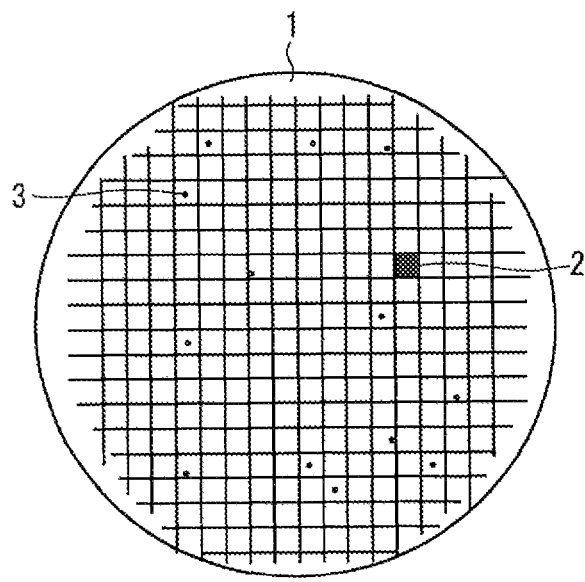

• DEFECT INSPECTION A
▲ DEFECT INSPECTION B
⊠ DEFECT INSPECTION C

DEFECT INSPECTION METHOD

BACKGROUND OF THE INVENTION

1. Field of the Invention

The present invention relates to a defect inspection method for inspecting a defect of a semiconductor wafer.

2. Description of the Background Art

In a method for controlling the quality and managing and improving the yield rate of a semiconductor wafer (hereinafter simply referred to as "wafer") in a semiconductor wafer process, it is essential to inspect a defect of the wafer in a main or important step included in the semiconductor wafer process, to thereby identify a foreign material and a defect in the wafer, manage a transition thereof, detect a process step including a problem, give a quick feedback, and the like.

In a semiconductor wafer process composed of a plurality of processes performed by many semiconductor manufacturing apparatuses, a defect that may adversely influence the characteristics occurs on a wafer during the preparation of a device (a chip obtained as a result of singulating the wafer) because of, for example, a foreign material existing in a clean room or in the apparatus used for each process, a damage to the wafer caused by performing many processes thereon, a pattern failure occurring in the formation of a pattern on the wafer, or the like. Such a defect causes a deterioration in the yield rate.

Additionally, in a wafer (such as a silicon carbide wafer (hereinafter also referred to as "SiC wafer") and a gallium nitride wafer (hereinafter also referred to as "GaN wafer")) having an inferior quality in which many substrate defects are contained, not all the defects cannot be detected and screened by a defect inspection included in the semiconductor wafer process, and there is a high possibility that some defects cannot be found by the detection. Therefore, a problem arises that an excessive burden is imposed on subsequent steps such as a testing step and a reliability evaluation step (that is, conditions required to be satisfied in these steps become excessively high), which greatly loweres the efficiency. In this manner, in a case where a wafer such as a SiC wafer and a GaN wafer having an inferior quality in which many defects are contained in the wafer itself is used in the semiconductor wafer process, the defects of the wafer itself may adversely influence the device characteristics. This causes a deterioration in the yield rate.

Moreover, if a wafer (device) having a defect that may influence the device characteristics cannot be selected in an electrical characteristics test and its failure is determined for the first time in a subsequent reliability test so that the wafer is selected at that time, time and labor are wastefully consumed for the failure device because the failure device has been formed through many processes. This causes an inefficiency in an inspection step of evaluating the electrical characteristics and the like.

Conventionally, there is a technique of inspecting the presence or absence of a defect on the wafer and marking a position where the defect is detected to thereby determine the good/poor of the device (for example, see Japanese Patent Application Laid-Open No. 63-222438 (1988)).

To improve the yield rate in the semiconductor wafer process, it is necessary that a defect of a wafer or a defect in each process that may influence the device characteristics is detected with a sufficient accuracy and then, based on a result of the detection, the wafer is rejected at an early stage or a feedback is given to the process in which the defect has occurred, in order to reduce defects. For this purpose, it is desirable that defect information obtained as a result of a defect inspection is grasped as electronic data on a chip basis.

In Japanese Patent Application Laid-Open No. 63-222438 (1988), a result obtained by a defect inspection is not dealt as electronic data. Moreover, the defect inspection is not performed on the wafer itself having an inferior quality mentioned above. Therefore, there is a possibility that a defect of the wafer itself adversely influences the device characteristics and causes a deterioration in the yield rate.

SUMMARY OF THE INVENTION

An object of the present invention is to provide a defect inspection method that allows defect information to be grasped on a chip basis and a defect to be detected at an early stage even if a wafer has an inferior quality in which many substrate defects are contained, to thereby improve the yield rate in a semiconductor wafer process.

A defect inspection method according to the present invention is a defect inspection method for inspecting a defect of a semiconductor wafer, including the steps of: (a) forming a mark on a semiconductor wafer that is an inspection object, the mark corresponding to the size of a device chip that will be obtained from the semiconductor wafer, the mark being formed with respect to a predetermined device chip on the semiconductor wafer; and (b) during a predetermined process included in a semiconductor wafer process or before the semiconductor wafer process, performing a defect inspection on the semiconductor wafer and recognizing defect information based on the mark as a reference.

The present invention includes the steps of: (a) forming a mark on a semiconductor wafer that is an inspection object, the mark corresponding the size of a chip that will be obtained from the semiconductor wafer, the mark being formed with respect to a predetermined chip on the semiconductor wafer; and (b) during a predetermined process included in a semiconductor wafer process or before the semiconductor wafer process, performing a defect inspection on the semiconductor wafer and recognizing defect information based on the mark as a reference. Accordingly, the defect information can be grasped on a chip basis, and even if a wafer has an inferior quality in which many substrate defects are contained, the defects can be detected at an early stage and the yield rate in the semiconductor wafer process can be improved.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a diagram showing one example of performing a defect inspection during a semiconductor wafer process according to a preferred embodiment 1 of the present invention;

FIG. 2 is a diagram showing one example of a map obtained as a result of the defect inspection on a semiconductor wafer according to the preferred embodiment 1 of the present invention;

DESCRIPTION OF THE PREFERRED EMBODIMENTS

In the following, some preferred embodiments of the present invention will be described with reference to the accompanying drawings.

Preferred Embodiment 1

FIG. 1 is a diagram showing one example of performing a defect inspection during a semiconductor wafer process (hereinafter also referred to as "wafer process") according to a preferred embodiment 1 of the present invention, and is a diagram showing the relationship between each process and a defect inspection, throughout a device preparation step including a semiconductor wafer process, an electrical characterization, and the like. This preferred embodiment 1 assumes a case where the defect inspection is performed by a microscope inspection using a normal lens.

As shown in FIG. 1, the defect inspection is performed in an arbitrary process (for example, a main or important process) included in the wafer process (process defect detections A and B in FIG. 1), and a foreign material, a pattern defect, and the like, occurring in each process are detected (see FIG. 2). In a case where the defect inspection is performed in a plurality of processes, it is possible to obtain a difference in the defects among the processes (see FIG. 4). A result of the defect inspection is fed back to each process. The defect inspection may also be performed on a semiconductor wafer itself (substrate) before the wafer process is started (substrate defect detection in FIG. 1). Details of the above-mentioned defect inspection will be described later.

Figure 3:
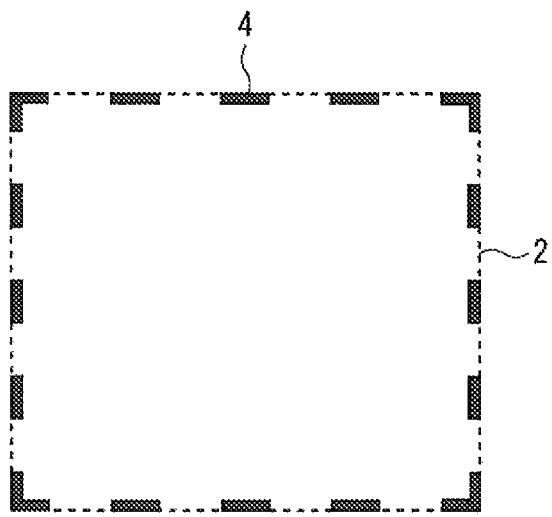
FIG. 3 is a diagram showing one example of a mark that is formed on the semiconductor wafer according to the preferred embodiment 1 of the present invention.

Next, a defect inspection method according to this preferred embodiment 1 will be described with reference to FIGS. 1 to 3.

FIG. 2 is a diagram showing one example of a map obtained as a result of the defect inspection on a semiconductor wafer 1 according to this preferred embodiment 1. FIG. 3 is a diagram showing one example of a mark 4 that is formed on the semiconductor wafer 1 according to this preferred embodiment 1.

Prior to performing the defect inspection, the mark 4 is formed on the semiconductor wafer 1. The mark 4 corresponds to the size of a device chip 2 (chip) which will be obtained from this semiconductor wafer 1, and the mark 4 is formed with respect to a predetermined device chip 2 (see FIG. 3). To be specific, for example, the mark 4 is formed with respect to the device chip 2 (black portion) shown in FIG. 2. The mark 4 is formed by, for example, etching, and serves as a reference based on which defect information is obtained at a time of the defect inspection. In this preferred embodiment, the mark 4 is formed on one arbitrary device chip 2, but may also be formed on a plurality of device chips 2. The shape of the mark 4 is not limited to the one shown in FIG. 3, as long as it corresponds to the size of the device chip 2.

Then, a predetermined wafer process (semiconductor wafer process) is performed on the semiconductor wafer 1 having the mark 4 formed thereon.

Then, the defect inspection is performed in an arbitrary process (for example, a main or important process) included in the wafer process, to detect a defect. Here, a case is assumed where the defect inspection is performed in one process (for example, either one of the process defect detections A and B in FIG. 1 is performed).

In the defect inspection, the outer shapes and positions of all the chips on the semiconductor wafer 1 are recognized based on one or more marks 4 as a reference. Thereby, the defect information (the position, size, and type of the defect) is grasped (obtained) on a unit basis of the size of the device chip 2. Thus, by performing the defect inspection, information including a defect position 3 on the semiconductor wafer 1 (or the device chip 2), and the like, can be grasped (recognized) as electronic data. For example, FIG. 2 shows a state where the defect positions 3 obtained as a result of the defect inspection are mapped on the semiconductor wafer 1. The information obtained as a result of the defect inspection includes not only the information about the defect position 3 but also visual information such as an image (photograph) of the defect.

Accordingly, performing the defect inspection in an arbitrary process included in the wafer process makes it possible to statistically grasp the position of a defect on the semiconductor wafer 1 (or the device chip 2), the type of the defect, and a process in which the defect occurs. Additionally, it is also possible to obtain the correlation between a chip having an electrical characteristics failure, which is found by evaluating the eventually-generated device chip 2 for its electrical characterization, and a defect occurring in the course of the wafer process. Moreover, by accumulating correlation data and feeding back the correlation data to each process, a device chip 2 that may be a failure chip can be screened at a stage of the wafer process. This can prevent the failure chip from being put on the market, and can enhance the speed and the efficiency of a testing step and a reliability evaluation step in which an electrical characterization, and the like, are performed.

Although the case where the defect inspection is performed in one process included in the wafer process has been described above, the defect inspection may be performed in a plurality of processes. For example, both of the process defect detections A and B shown in FIG. 1 may be performed.

Figure 4:
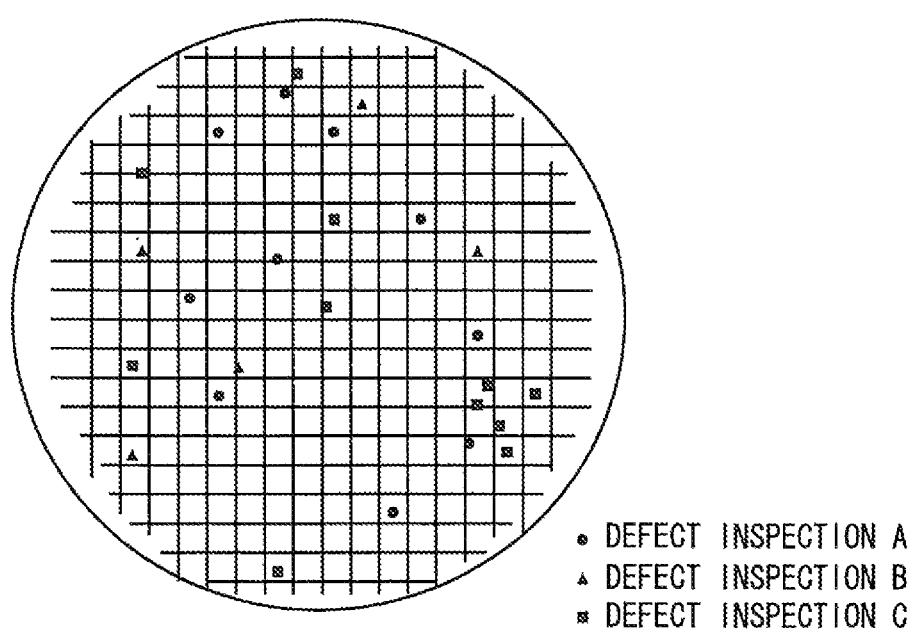
FIG. 4 is a diagram showing one example of a map obtained as a result of the defect inspection according to the preferred embodiment 1 of the present invention, in a case where a plurality of defect inspections are performed.

FIG. 4 is a diagram showing one example of a map obtained as a result of the defect inspection according to this preferred embodiment 1, in a case where a plurality of defect inspections are performed. FIG. 4 shows a state where the defect inspection results as shown in FIG. 2 corresponding to a plurality of processes, respectively, are superimposed on one another. For example, as shown in FIG. 4, defect inspections A, B, and C are performed in the plurality of processes, and results of the inspections are superimposed on one another and mapped on the semiconductor wafer 1.

Accordingly, by performing the defect inspections in a plurality of processes included in the wafer process, information about a transition of the defect through the plurality of processes can be obtained. Therefore, an inspection in a subsequent step can be performed under the condition that a device chip that has been identified as failure one (with a fatal defect) is deselected in advance. This can shorten a time required for performing the inspection in the subsequent step. Additionally, obtaining a difference in the defects among the plurality of defect inspections (the plurality of processes) makes it possible to discover a process malfunction (a process in which many defects occur) at an early stage, to prevent a failure chip from being put on the market, and to feed back malfunction information to each process. Moreover, by deselecting a device chip that may cause a failure in advance, efficient evaluations can be made in an electrical characterization and a reliability evaluation that are performed after the wafer process is completed.

In the above, the case where the defect inspections are performed in the plurality of processes included in the wafer process has been described. Here, for the purpose of clarifying the identify of the semiconductor wafer 1, inspection results obtained by the inspection (defect inspection) of the semiconductor wafer itself, which is performed before the wafer process, may be mapped on a device-chip basis. The inspection (defect inspection) of the semiconductor wafer itself includes, for example, a wafer concentration inspection, a wafer thickness inspection, and a wafer resistivity inspection.

As described above, if a wafer (such as a SiC wafer or a GaN wafer) having an inferior quality in which many defects are contained is used in the semiconductor wafer process, the defects of the wafer itself may adversely influence the device characteristics, which may cause a deterioration in the yield rate. Thus, defects of the semiconductor wafer 1 itself are inspected before the wafer process, and inspection results thereof are superimposed, to thereby allow a supposition of a failure chip based on a theoretical accumulation. Additionally, by selecting and deselecting such a failure chip in advance, the efficiency of each process is improved. Here, the mark 4 is formed in advance before the defect inspection is performed on the semiconductor wafer 1 itself, and at a time of the defect inspection, the defect information is obtained (recognized) based on the mark 4 as a reference.

Accordingly, in this preferred embodiment 1, even if a wafer has an inferior quality in which many substrate defects are contained, a device chip (failure chip) that may be regarded as a fatal defect is detected and screened at an early stage prior to a testing step (such as an electrical characterization), and thereby the efficiency of the testing step and the reliability evaluation can be enhanced, to improve the yield rate in the wafer process. Additionally, throughout the device preparation, an efficient process management, an efficient screening, and an efficient evaluation are achieved.

Preferred Embodiment 2

In the preferred embodiment 1, the defect inspection is performed by the microscope inspection using the normal lens. In this preferred embodiment 2, the defect inspection is performed by a defect inspection apparatus with a differential interference contrast technique. Except for this point, the configuration and operation are the same as those of the preferred embodiment 1, and therefore descriptions thereof are omitted here.

Using the defect inspection apparatus with the differential interference contrast technique can detect, with a high accuracy, a defect having a low degree of irregularities in a surface of the semiconductor wafer (substrate), which is difficult to detect by the microscope inspection according to the preferred embodiment 1. Therefore, this is effective particularly to a semiconductor wafer having defects in the shape of fine irregularities. Accordingly, for example, in a substrate defect inspection (the defect inspection performed on the semiconductor wafer itself before the wafer process), a defect (such as step-bunching or pits) originating from the semiconductor wafer itself can be grasped on a device-chip basis. Thus, at this stage (substrate defect inspection stage), a device chip containing a fatal defect that may influence the device can be selected and deselected.

Accordingly, in this preferred embodiment 2, the accuracy of detection of a defect existing in the semiconductor wafer is enhanced. Thus, a device chip containing a defect that may eventually cause a failure in the device characteristics or that may eventually be evaluated as a failure in the reliability test can be deselected at an early stage, that is, at the substrate defect inspection stage. Thus, the efficiency of the evaluation, the testing, and the like, is enhanced.

The preferred embodiments of the present invention can be combined in any manner and can be modified or omitted as appropriate as long as it is within the scope of the invention.

While the invention has been shown and described in detail, the foregoing description is in all aspects illustrative and not restrictive. It is therefore understood that numerous modifications and variations can be devised without departing from the scope of the invention.

What is claimed is:

1. A defect inspection method for inspecting a defect of a semiconductor wafer, said method comprising the steps of:
    (a) forming a reference mark on a semiconductor wafer that is an inspection object, said reference mark corresponding to the size of a chip that will be obtained from said semiconductor wafer such that the size of the chip can be recognized based on the reference mark, said reference mark being formed with respect to a predetermined chip on said semiconductor wafer; and
    (b) during a predetermined process included in a semiconductor wafer process or before said semiconductor wafer process, performing a defect inspection on said semiconductor wafer and recognizing defect information based on said mark as a reference.

2. The defect inspection method according to claim 1, wherein in said step (b), said defect information is recognized on a chip basis.

3. The defect inspection method according to claim 1, wherein in said step (b), said defect inspection is performed in a plurality of processes included in said semiconductor wafer process.

4. The defect inspection method according to claim 1, wherein in said step (b), said defect inspection is performed by using a differential interference contrast technique.

5. The defect inspection method according to claim 1, wherein said semiconductor wafer is a SiC wafer or a GaN wafer.

6. A defect inspection method for inspecting a defect of a semiconductor wafer, said method comprising the steps of:
    (a) forming a reference mark on a semiconductor wafer that is an inspection object, said reference mark corresponding to the size of a chip that will be obtained from said semiconductor wafer such that outer shape and position of the chip can be recognized based on said reference mark, said reference mark being formed with respect to a predetermined chip on said semiconductor wafer; and
    (b) during a predetermined process included in a semiconductor wafer process or before said semiconductor wafer process, performing a defect inspection on said semiconductor wafer and recognizing defect information based on said mark as a reference.

7. The defect inspection method according to claim 6, wherein in said step (b), said defect information is recognized on a chip basis.

8. The defect inspection method according to claim 6, wherein in said step (b), said defect inspection is performed in a plurality of processes included in said semiconductor wafer process.

9. The defect inspection method according to claim 6, wherein in said step (b), said defect inspection is performed by using a differential interference contrast technique.

10. The defect inspection method according to claim 6, wherein said semiconductor wafer is a SiC wafer or a GaN wafer.

* * * * *